April 30, 1946. H. R. BOHANNON Plant Pat. 684
GERANIUM PLANT
Filed July 11, 1945
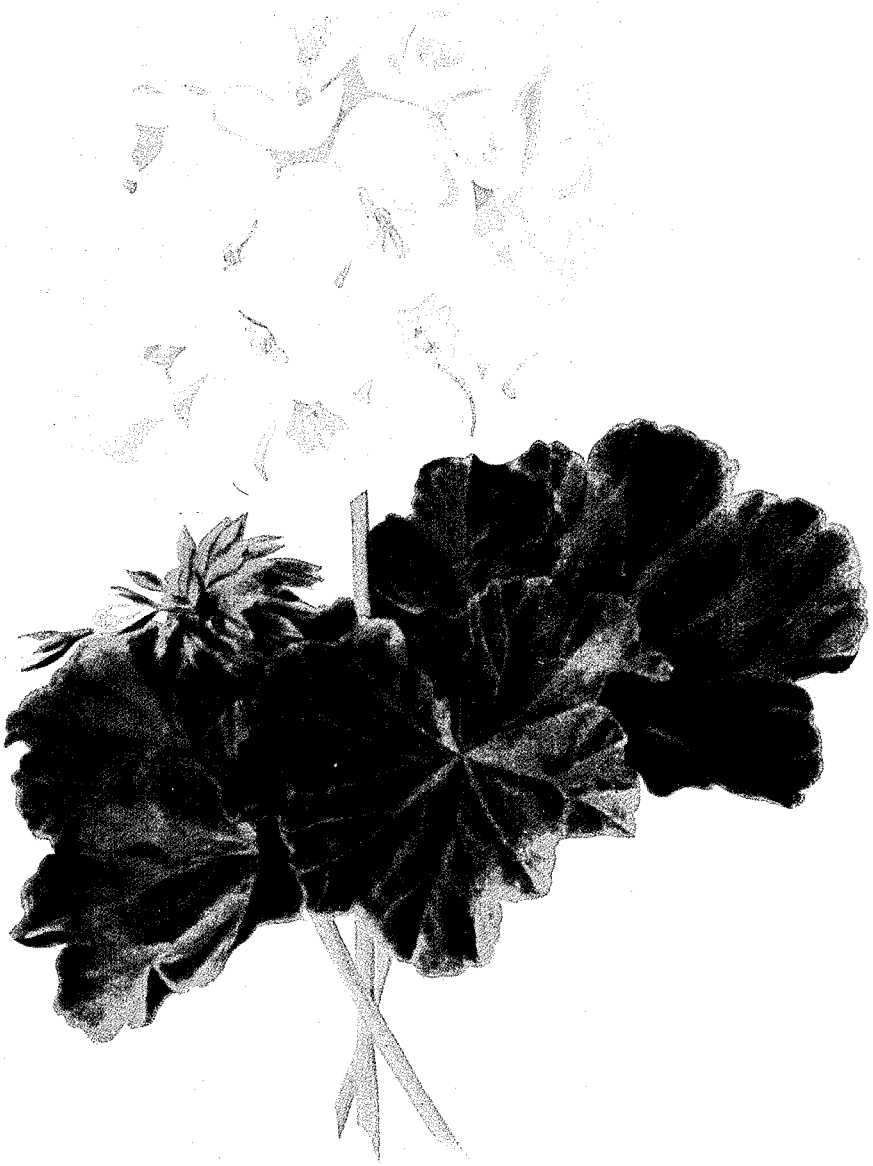
INVENTOR
Helen Roberta Bohannon
By Orville M. Kile
Plant Pat. Agt.

Patented Apr. 30, 1946

Plant Pat. 684

UNITED STATES PATENT OFFICE

684

GERANIUM PLANT

Helen Roberts Bohannon, Berkeley, Calif., assignor to Paul J. Howard Company, and Paul J. Howard's California Flowerland, Los Angeles, Calif., a corporation of California Application July 11, 1945, Serial No. 604,388

1 Claim. (Cl. 47—60)

My present invention relates to a new and improved variety of geranium plant and is the result of definite breeding efforts carried on by me in connection with attempts to produce varieties of the general type of Nouvelle Aurore but with a hardier constitution. I crossed Nouvelle Aurore with an unnamed seedling, then took one of the first year crosses and back-crossed it with Nouvelle Aurore. The present variety is the result of one of these back crosses and is the first of a series of desirable varieties.

This new variety is a continuous and very prolific bloomer and the florets are very large and of "pansy form," with color of pleasing pastel.

Accompanying illustrations show a truss of florets, together with buds and foliage of this new variety, which in the original are shown approximately in their true size and colors.

Following is a description of the flower and plant of this new variety of geranium. Color names refer to the Horticultural Colour Chart except where otherwise indicated.

*The plant*

Growth: Very vigorous and compact. Attains an average height of 12 to 18 inches when grown as a pot plant and 2 feet or more when grown outdoors in southern California climate.

Blooming habit: Very free and continuous bloomer both outdoors and as a pot plant. Grown in 4-inch pots a plant produces 2 or 3 trusses at one time, while a full grown plant produces 40 to 50 trusses at one time.

Inflorescence: Large, compact umbel or truss.

Foliage:

*Quantity.*—Abundant.

*Size.*—Average to large, approximately 3 to 3½ inches in diameter.

*Color.*—Spinach Green (Pl. V, Ridgway's).

*Shape.*—Disk-shaped and undulating, with deep-lobed edges.

*Texture and aspect.*—Firm; thick; upper surface smooth; lower surface moderately hairy.

Stem: Long and strong.

Petiole: Strong; slightly hairy.

Peduncle: Strong; heavy; slightly hairy; color same as foliage.

*The flower*

Truss:

*Size.*—Large, measuring 5½ to 6 inches in diameter.

*Shape.*—Compact and globular.

*Number of florets.*—Average to a truss 20 to 25.

*Lasting quality.*—Remains in bloom 10 days to 2 weeks.

Bud:

*Sepals.*—Long and pointed.

*Color.*—Vermillion (18).

*Form.*—Pointed.

Florets:

*Size.*—Average about 2 inches in diameter.

*Petalage.*—Single, with 5 petals.

*Color.*—Vermillion (18/1) at edges of petals, lightening to Vermillion (18/2) toward the center and merging into a large white eye in center of floret. Center markings are Carmine (21) to (21/2). Color is retained without fading.

*Texture and aspect.*—Firm and glistening.

*Form.*—Petals are smooth edged and overlapping in pansy-like effect. When all florets are open the globular truss is very compact.

*Lasting quality.*—Average floret lasts 2 to 3 days.

*Behavior.*—Petals drop cleanly, do not die on stem.

Having thus disclosed my invention, I claim:

The new and useful variety of geranium plant substantially as shown and described, characterized particularly by its healthy growth; its continuous and exceptionally free blooming habit; its compact globular truss of great size; its large pansy-like florets with overlapping petals which drop cleanly when dead; and the distinctive color of its flower ranging from Vermillion to Carmine except for the white eye.

HELEN ROBERTS BOHANNON.